United States Patent
Kishimoto

(10) Patent No.: US 9,962,289 B2
(45) Date of Patent: May 8, 2018

(54) FRAGMENTATION TIP, INTRAOCULAR SURGERY DEVICE PROVIDED WITH SAME, METHOD FOR SUPPRESSING OCCURRENCE OF CAVITATION, AND CATARACT SURGERY METHOD

(75) Inventor: Makoto Kishimoto, Moriyama (JP)

(73) Assignee: SENJU PHARMACEUTICAL CO., LTD., Osaka-shi (JP)

( * ) Notice: Subject to any disclaimer, the term of this patent is extended or adjusted under 35 U.S.C. 154(b) by 310 days.

(21) Appl. No.: 14/372,158

(22) PCT Filed: Apr. 18, 2012

(86) PCT No.: PCT/JP2012/060484
§ 371 (c)(1),
(2), (4) Date: Jul. 16, 2014

(87) PCT Pub. No.: WO2013/125056
PCT Pub. Date: Aug. 29, 2013

(65) Prior Publication Data
US 2015/0073459 A1 Mar. 12, 2015

(30) Foreign Application Priority Data
Feb. 20, 2012 (JP) ................................ 2012-034462

(51) Int. Cl.
*A61F 9/00* (2006.01)
*A61F 9/007* (2006.01)
*A61B 17/32* (2006.01)

(52) U.S. Cl.
CPC .............. *A61F 9/00745* (2013.01); *A61B 2017/32008* (2013.01); *A61B 2017/320072* (2013.01);
(Continued)

(58) Field of Classification Search
CPC .............. A61F 9/00745; A61F 9/00736; A61F 9/00754; A61F 9/00763; A61F 17/320016; A61F 17/320068
See application file for complete search history.

(56) References Cited

U.S. PATENT DOCUMENTS 4,861,332 A 8/1989 Parisi
6,007,555 A 12/1999 Devine
(Continued)

FOREIGN PATENT DOCUMENTS

CN 102186423 A 9/2011
EP 1700584 A1 9/2006
(Continued)

OTHER PUBLICATIONS

International Search Report issued in PCT/JP2012/060484, dated May 29, 2012.
(Continued)

Primary Examiner — Katrina Stransky
Assistant Examiner — Kankindi Rwego
(74) Attorney, Agent, or Firm — Fox Rothschild LLP

(57) ABSTRACT

Provided is a fragmentation tip, an intraocular surgery device, a method for suppressing an occurrence of cavitation, and a cataract surgery method, which can suppress the occurrence of cavitation. The fragmentation tip, which is attached to an intraocular surgery device configured to apply ultrasonic vibration, includes: a cylindrical support portion configured to be mounted on the intraocular surgery device; and a cylindrical tip body provided at a distal end of the support portion to be in communication with an internal space of the support portion, wherein the tip body has a cross sectional shape having a length in a first direction that is larger than a length in a second direction that is orthogonal to the first direction, and vibration is applied to the support (Continued)

portion so that the tip body rotates back and forth about an axis of the tip body that passes through its center in the first and second directions.

5 Claims, 10 Drawing Sheets

(52) U.S. Cl.
CPC ............. *A61B 2017/320098* (2017.08); *A61B 2217/007* (2013.01)

(56) References Cited

U.S. PATENT DOCUMENTS

| | | |
|---|---|---|
| 2005/0187513 A1 | 8/2005 | Rabiner et al. |
| 2006/0217672 A1 | 9/2006 | Chon |
| 2008/0058708 A1* | 3/2008 | Akahoshi ............ A61F 9/00745 604/22 |
| 2008/0103430 A1 | 5/2008 | Gomez |
| 2009/0099536 A1 | 4/2009 | Akahoshi |
| 2011/0112466 A1 | 5/2011 | Dimalanta |

FOREIGN PATENT DOCUMENTS

| | | |
|---|---|---|
| JP | 2004-305682 A | 11/2004 |
| JP | 2006-247392 A | 9/2006 |
| WO | WO-2010/022460 A1 | 3/2010 |
| WO | 2011/059597 A1 | 5/2011 |
| WO | 2011120080 A1 | 10/2011 |

OTHER PUBLICATIONS

Office Action issued in Chinese Patent Application No. 201280070248.4, dated Jul. 28, 2015.
Office Action dated Feb. 26, 2016 issued in the corresponding Russian Patent Application No. 2014138043.
Office Action issued in Chinese Patent Application No. 2014-500848, dated Nov. 17, 2015.
Office Action issued in the corresponding Chinese Patent Application No. 201280070248.4 dated Mar. 21, 2016.
Office Action issued in the counterpart Mexican Patent Application No. MX/A/2014/009987 dispatched on Apr. 4, 2017.
Office Action issued in the counterpart Mexican Patent Application No. MX/A/2014/009987 dispatched on Sep. 22, 2016.

* cited by examiner

FRAGMENTATION TIP, INTRAOCULAR SURGERY DEVICE PROVIDED WITH SAME, METHOD FOR SUPPRESSING OCCURRENCE OF CAVITATION, AND CATARACT SURGERY METHOD

TECHNICAL FIELD

The present invention relates to a fragmentation tip, an intraocular surgery device provided with the same, a method for suppressing an occurrence of cavitation, and a cataract surgery method.

BACKGROUND ART

In recent years, operations to replace a crystalline lens with an intraocular lens (artificial lens) have been widely employed for eye diseases such as cataract. As one of such operations, phacoemulsification and aspiration (PEA) surgery in which an eye lens in an affected area is fragmented and emulsified by ultrasonic vibration and the lens nucleus is aspirated has been widely adopted. In this surgery, an ultrasonic handpiece (which may be hereinafter referred to simply as "handpiece") that is an ultrasonic emulsification and aspiration device is used. The handpiece includes a rod shaped body that is supported by a hand of an operator, an oscillator that generates ultrasonic vibration, and a horn that amplifies the ultrasonic vibration generated by the oscillator. The oscillator and the horn are incorporated in the body. A fragmentation tip for fragmenting and emulsifying a lens nucleus is mounted on the distal end of the body. The tubular fragmentation tip is coupled to the horn, and is capable of applying ultrasonic vibration to a lens nucleus that is targeted in the surgery in surgery while an irrigation solution is supplied to an anterior chamber of an eye, the nucleus is fragmented and emulsified by ultrasonic vibration. The emulsified nucleus is discharged via an aspiration channel provided in the handpiece, together with the irrigation solution. Fragmentation tips for fragmentation of a lens nucleus in various shapes have been proposed. For example, there is a flattened type as in Patent Literature 1.

CITATION LIST

Patent Literature

[PTL 1] JP 2004-305682 A

SUMMARY OF INVENTION

Technical Problem

As shown in FIG. 14(*a*), a common fragmentation tip such as a fragmentation tip 100 is formed into a cylindrical shape, and is configured to fragment a lens nucleus by being moved forward and backward by ultrasonic vibration. At this time, the fragmentation tip 100 is moved back and forth in an irrigation solution. However, the fragmentation tip is separated from the irrigation solution when the fragmentation tip 100 moves back, as shown in FIG. 14(*b*). Therefore, a negative pressure is generated in the vicinity of the distal end of the fragmentation tip. When such a negative pressure is generated, the boiling point of the irrigation solution is lowered in the vicinity of the distal end of the fragmentation tip, thereby causing a phenomenon, so-called cavitation, in which air bubbles are generated due to boiling of the irrigation solution. Such cavitation may possibly damage the iris or endothelial cells, though not having such a force to emulsify the nucleus. Further, such cavitation is a problem which can occur not only in a fragmentation tip that moves linearly forward and backward but also in a fragmentation tip that rotates back and forth.

The present invention has been devised to solve the aforementioned problem, and an object thereof is to provide a fragmentation tip, an intraocular surgery device, a method for suppressing an occurrence of cavitation, and a cataract surgery method, which are capable of suppressing the occurrence of cavitation.

Solution to Problem

A fragmentation tip according to the present invention, which is attached to an intraocular surgery device configured to apply ultrasonic vibration, includes: a cylindrical support portion configured to be mounted on the intraocular surgery device; and a cylindrical tip body provided at a distal end of the support portion so as to be in communication with an internal space of the support portion, wherein the tip body has a cross sectional shape having a length in a first direction larger than a length in a second direction that is orthogonal to the first direction, and vibration is applied to the support portion so that the tip body rotates back and forth about an axis of the tip body that passes through its center in the first direction and the second direction.

According to this configuration, the following effects, for example can be obtained when fragmenting a lens nucleus in a cataract surgery. The back-and-forth rotation of the tip body is herein described, where a rotation in one direction is referred to as rotation in the positive direction, and a rotation in the opposite direction is referred to as rotation in the reverse direction. First, the tip body according to the present invention has a cross section having a length in the first direction larger than a length in the second direction. Therefore, as the fragmentation tip rotates in the positive direction, one end in the circumferential direction of a surface along the first direction rotates so as to press the irrigation solution. Thus, a positive pressure is generated in this region. On the other hand, the other end in the circumferential direction of the surface along the first direction rotates so as to move away from the irrigation solution. Thus, as negative pressure is generated in this region. However, the irrigation solution pressed by the aforementioned one end flows toward the other end side with the rotation of the tip body and therefore the negative pressure generated on the other end side is eliminated. As a result, the occurrence of cavitation is suppressed. On the other hand, when the fragmentation tip rotates in the reverse direction, the same phenomenon occurs. That is, in the case of the rotation in the reverse direction, a negative pressure is generated at one end of the surface along the first direction. However, the irrigation solution flows from the other end to one end side, in the same manner as above, and therefore the negative pressure is eliminated. Accordingly the fragmentation tip according to the present invention can suppress the occurrence of cavitation even if the back-and-forth rotation is repeated. It should be noted that the rotational center of the aforementioned back-and-forth rotation is not necessarily strictly at the center of the tip body in the first direction and the second direction, and may deviate to some extent, as long as the occurrence of cavitation is suppressed.

Further, the tip body has a cross sectional shape that is narrow in the first direction, as described above, thereby allowing the fragmentation tip to be easily inserted into the nucleus. That is, since nuclear fibers of the nucleus extend in a predetermined direction, the fragmentation tip can be easily inserted with less resistance by being inserted along the nuclear fibers. Therefore, the present invention can facilitate the insertion into the nucleus by forming the tip body as described above, as compared to the case of forming the tip body into a square shape. From such a viewpoint, the tip body preferably has a length in the first direction that is two or more times the length in the second direction, for example.

The aforementioned cross section of the tip body can be of various shapes in which the length in the first direction is larger than the length in the second direction that is orthogonal to the first direction. However, the tip body preferably has an cross sectional shape that is linearly symmetrical, and further preferably has a point-symmetrical cross sectional shape, for example. Specifically, a rectangular shape, an ellipsoidal shape, and a rhombic shape can be employed, for example.

If the fragmentation tip according to the present invention has a rectangular cross section, the tip body may be formed so that the first surface and the second surface extending along the first direction oppose each other, and the third surface and the fourth surface extending along the second direction oppose each other.

Such a configuration allows projections (corners) projecting outwardly in the radial direction to be formed at both ends of the first surface and the second surface. Accordingly for example, when the fragmentation tip rotates in the positive direction, the projections of the first surface and the second surface on one end side rotate so as to press the irrigation solution, thereby applying shock to the nucleus in these portions. On the other hand, when the fragmentation tip rotates in the reverse direction, the projections of the first surface and the second surface on the other end side rotate so as to press the irrigation solution, thereby applying shock to the nucleus in these portions. That is one time of back-and-forth rotation can apply shock to the nucleus in four portions, and thus it is possible to fragment the nucleus efficiently.

Recessed portions may be formed on the first surface and the second surface. Such a configuration allows the irrigation solution pressed, for example, by one end in the circumferential direction of the first surface to flow into such as recessed portion with the rotation, and to flow toward the other end side via the recessed portion. Therefore, it is easier for the irrigation solution to flow from one end side to the other end side. As a result, the negative pressure on the other end side is easier to eliminate. Also in the rotation in the reverse direction, formation of recessed portions can facilitate the flow of the irrigation solution from the other end side to one end side, in the same manner as above. Accordingly, it is possible to further prevent the occurrence of negative pressure and thereby reliably suppress the occurrence of cavitation.

The recessed portions of the first surface and the second surface may be formed into an arcuate shape. Such a configuration allows the irrigation solution to flow smoothly, for example, from one end side to the other end side of the first surface and the second surface so that the aforementioned negative pressure is eliminated.

Further, arcuate protruding portions may be provided on the third surface and the fourth surface. Such a configuration allows the outlines of the arcuate protruding portions to lie along the rotational direction when the fragmentation tip rotates, and thus can prevent an increase in resistance to the irrigation solution in these portions.

When forming recessed portions in any one of the aforementioned fragmentation tips, the depth of each recessed portion is preferably 1 to 40%, further preferably 2 to 40%, of the length in the second direction of the tip body.

Further, in any one of the aforementioned fragmentation tips, the length in the long side direction of the recessed portions can be 10 to 60% of the length in the first direction of the tip body.

An intraocular surgery device according to the present invention includes: a body configured to be supported by a hand of an operator; a vibration generator incorporated in the body and configured to generate ultrasonic vibration; and any one of the aforementioned fragmentation tips which is configured to be coupled to a distal end of the body so as to be vibrated by the vibration generator, wherein vibration is applied to the fragmentation tip by the vibration generator so that the fragmentation tip rotates back and forth about the center of point symmetry.

A method for suppressing an occurrence of cavitation according to the present invention includes: a step of preparing any one of the aforementioned fragmentation tips; and a step of applying infrasonic vibration to the fragmentation tip so that the tip body rotates back and forth about the axis of the tip body that passes through its center in the first direction and the second direction.

A cataract surgery method according to the present invention includes: a step of attaching any one of the aforementioned fragmentation tips to an intraocular surgery device configured to apply ultrasonic vibration; a step of applying ultrasonic vibration to the fragmentation tip so that the tip body rotates forward and backward about the axis of the tip body that passes through its center in the first direction and the second direction; and a step of fragmenting a nucleus of lens of a cataract patient by applying shock to the nucleus using the fragmentation tip, while supplying an irrigation solution to the eye of the patient.

Effect of Invention

According to the present invention, it is possible to suppress the occurrence of cavitation.

DESCRIPTION OF EMBODIMENTS

Hereinafter, a fragmentation tip and a handpiece on which the fragmentation tip is mounted (intraocular surgery device) are described as an embodiment of the present invention with reference to the drawings. First, an embodiment of the handpiece will be described, and thereafter two embodiments of the fragmentation tip will be described.

Handpiece

Figure 1:
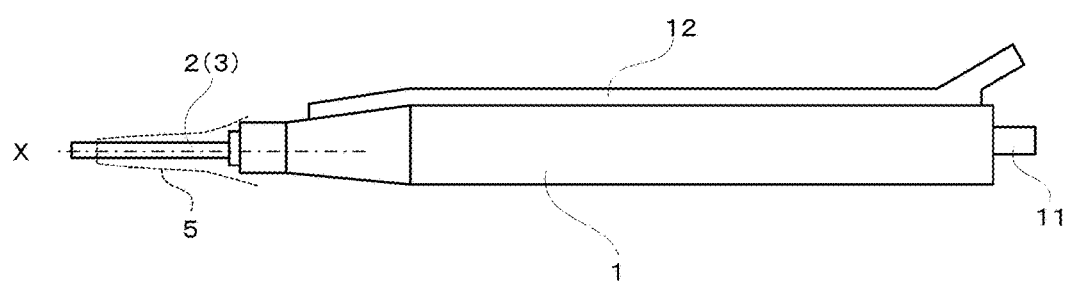
FIG. 1 is a side view of a handpiece according to an embodiment of the present invention.

FIG. 1 is a side view of a handpiece. As shown in this figure, a handpiece according to this embodiment is formed into a cylindrical shape, and includes a body 1 that is held by a hand of an operator. An oscillator (not shown) that generates ultrasonic vibration and a horn (not shown) that amplifies the ultrasonic vibration generated by the oscillator are incorporated in the body 1. A tubular fragmentation tip 2 for fragmenting and emulsifying a lens nucleus is mounted on the distal end of the body 1, and a cylindrical sleeve 5 formed of a soft material such as silicon is arranged so as to cover the periphery of the fragmentation tip 2. The sleeve 5 is provided for preventing portions of the fragmentation tip 2 other than the distal end from coming into contact with an affected area, and the fragmentation tip 2 slightly projects from the distal end of the sleeve 5. In the following description and figures, the sleeve 5 may be omitted in some cases. The fragmentation tip 2 is coupled to the horn inside the body 1 and is capable of applying ultrasonic vibration to a lens nucleus that is targeted in the surgery. Vibration is applied to the fragmentation tip 2 so that it rotates back and forth about the axis of the tube (about the axis X, which will be described below). For example, vibration can be applied so that the fragmentation tip 2 rotates back and forth 30,000 to 40,000 times per minute at a rotation angle of 2 to 4 degrees. Further, a supply channel 12 for an irrigation solution extending toward the distal end side is provided on the outer circumferential surface of the body 1, so that the irrigation solution can be supplied from the vicinity of the fragmentation tip 2 to an anterior chamber of an eye. Further, the fragmentation tip 2 has a tubular shape, and therefore can aspirate the fragmented nucleus together with the irrigation solution. The aspirated nucleus is discharged to the outside from a port 11 at the back end of the body 1 through an aspiration channel incorporated in the body 1.

Fragmentation Tip: First Embodiment

Figure 2:
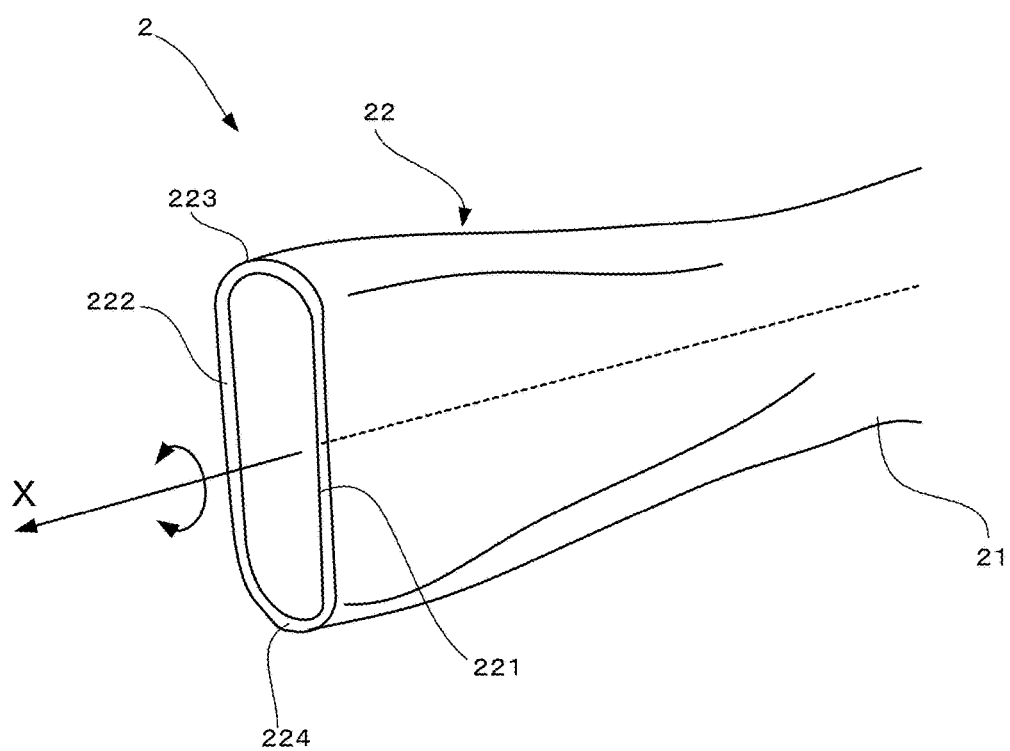
FIG. 2 is a perspective view showing a first embodiment of a fragmentation tip configured to be mounted on the handpiece in FIG. 1.
Figure 3:
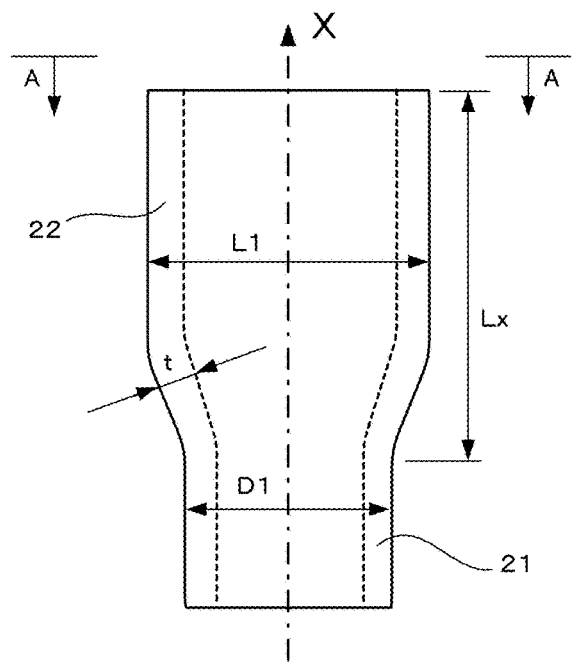
FIG. 3 is a side view of the fragmentation tip in FIG. 2.
Figure 4:
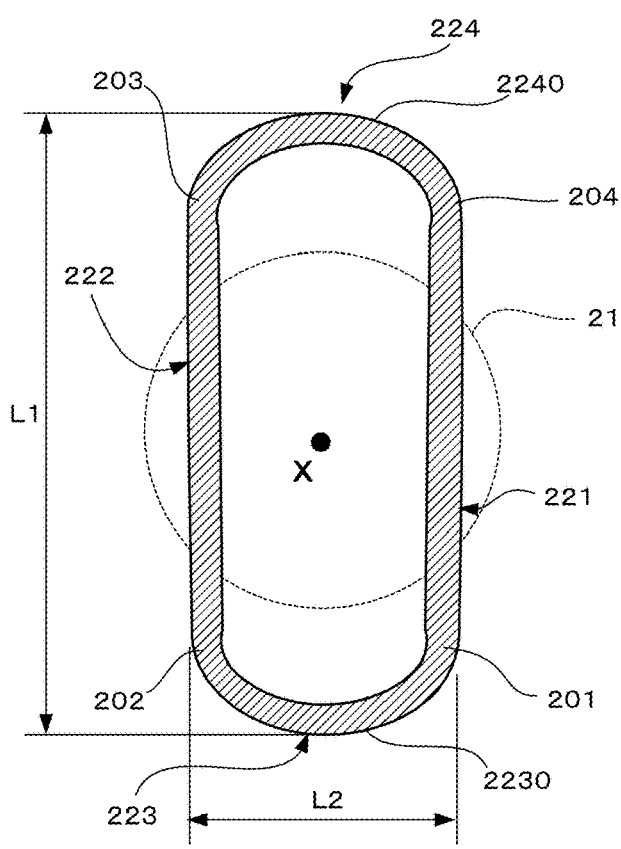
FIG. 4 is a view taken along the line A-A in FIG. 3 as seen in the direction of the arrows.

Next, a first embodiment of the fragmentation tip 2 will be described in detail with reference to FIG. 2 to FIG. 4. FIG. 2 is a perspective view of the fragmentation tip, FIG. 3 is a side view of FIG. 2, and FIG. 4 is a view taken along the line A-A in FIG. 3 as seen in the direction of the arrows. Hereinafter, the direction in which the fragmentation tip 2 extends from the body 1 will be referred to as axis direction X, and the direction that extends radially from the axis will be referred to as the radial direction.

As shown in FIG. 2, the fragmentation tip 2 is formed of metal, or the like, and is composed of a support portion 21 that is attached to the distal end of a body 11 and extends cylindrically, and a tip body 22 that is integrally attached to the distal end of the support portion 21 and is configured to fragment a lens nucleus. The support portion 21 and the tip body 22 are formed together into a tubular shape as a whole, as described above, through which the fragmented nucleus and the irrigation solution pass. That is, a flow channel that extends from the opening at the distal end of the tip body 22 through the tip body 22 and the support portion 21, is formed.

The tip body 22 is formed into an approximate rectangular cuboid having a rectangular point-symmetrical cross section, and the aforementioned axis X extends through the center of the rectangular cross section (center of point symmetry). Here, opposing surfaces corresponding to the long sides of the rectangular shape are referred to as a first surface 221 and a second surface 222, and opposing surfaces corresponding to the short sides thereof are referred to as a third surface 223 and a fourth surface 224. Further, as shown in FIG. 3 and FIG. 4, a long side length (length in a first direction) L1 is formed to be larger than a diameter D1 of the support portion 21, and a short side length (length in a second direction) L2 is formed to be smaller than the diameter D1 of the support portion 21. Further, a material thickness t of the tip body 22 and the support portion 21 may be approximately constant or may be varied. The size of the tip body 22 is appropriately determined depending on the surgical form. For example, the long side length L1 may be 0.9 to 1.727 mm, and the short side length L2 may be 0.24 to 1.1 mm. Further, a length Lx of the tip body 22 in its axis direction, for example, may be 1 to 5 mm.

Next, the cross sectional shape of the tip body 22 is described further in detail with reference to FIG. 4. First, as shown in this figure, the long side length L1 is preferably about 1 to 7 times, and further preferably 2 to 5 times, the short side length L2. This is because if the cross section of the tip body 22 is a square-like shape, it is difficult to insert the tip body 22 into nuclear fibers of the n On the other hand, this is also because, in the case of an excessively narrow shape, processing is difficult and aspiration of the irrigation solution is also difficult. On the third surface 223 and the fourth surface 224, arcuate protruding portions 2230 and 2240 projecting outwardly in the radial direction are respectively formed. Further, coupled portions of adjacent surfaces form corners (projections) that project outwardly in the radial direction. Here, the coupled portion between the first surface 221 and the third surface 223 is referred to as a first corner 201, the coupled portion between the third surface 223 and the second surface 222 is referred to as a second corner 202, the coupled portion between the second surface 222 and the fourth surface 224 is referred to as a third corner 203, and the coupled portion between the fourth surface 224 and the first surface 221 is referred to as a fourth corner 204.

Next, a cataract surgery method using a handpiece configured as above is described. A cataract surgery is mainly composed of the following four steps. That is, there are steps of (1) incision of anterior capsule, (2) emulsification and aspiration of nucleus, (3) aspiration of cortex, and (4) insertion of intraocular lens, among which steps (1) and (2) are mainly described herein. First, in step (1), while maintaining the shape of the anterior chamber, for example, using a viscoelastic material, the anterior capsule is incised. In step (2), incision layers are formed in the cornea or sclera, and the fragmentation tip 2 is inserted into the anterior chamber, so that the nucleus is fragmented and emulsified by the vibration of the fragmentation tip 2. The emulsified nucleus is aspirated through the opening at the distal end of the fragmentation tip 2 together with the irrigation solution, and is discharged to the outside from the port 11 through the discharge channel in the handpiece. The anterior chamber is kept stable by maintaining a balance between the inflow amount of the irrigation solution and the aspiration amount.

Figure 5:
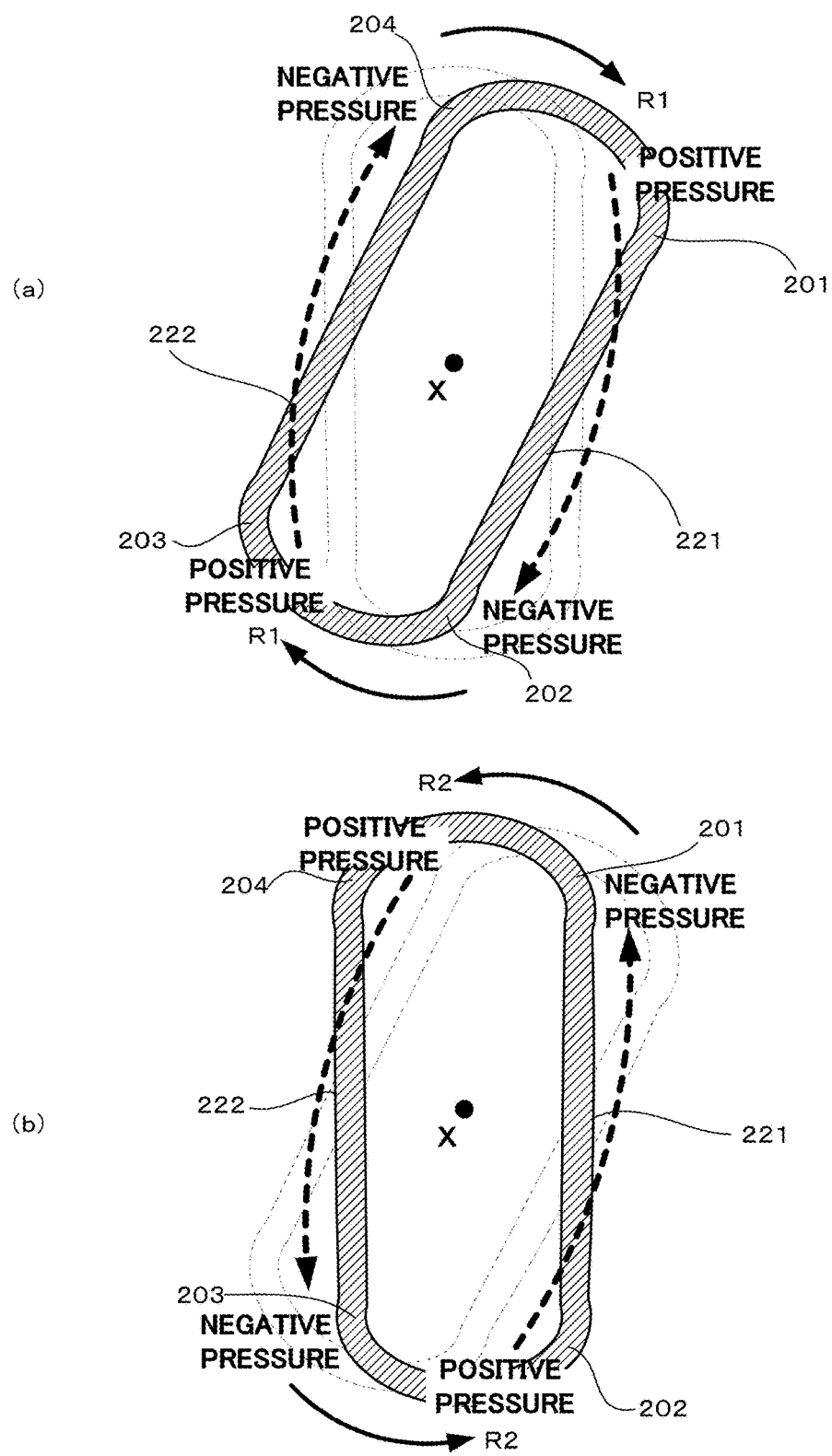
FIG. 5 is an explanatory diagram illustrating a movement, of the fragmentation tip in FIG. 2.

Subsequently, the movement of the fragmentation tip 2 will be described with reference to FIG. 5. Hereinafter, the clockwise direction in FIG. 5 will be referred to as positive direction R1, and the counterclockwise direction will be referred to as reverse direction R2. As described above, when ultrasonic vibration is applied to the fragmentation tip 2, the fragmentation tip rotates back and forth about the axis X. Specifically, the fragmentation tip rotates in the positive direction R1 at the aforementioned angle, thereby transferring the state from the state of FIG. 4 to the state of FIG. 5(a), and then the fragmentation tip rotates in the reverse direction R2 at the same angle, thereby transferring the state from the state of FIG. 5(a) to the state of FIG. 5(b), and this movement is repeated. First, when the fragmentation tip 2 rotates in the positive direction R1 from the state of FIG. 4 to the state of FIG. 5(a), one end of the first surface 221, that is, the first corner 201 rotates so as to press the irrigation solution, which causes a positive pressure in this region. On the other hand, the other end of the first surface 221, that is, the second corner 202 moves in a direction away from the irrigation solution, which causes a negative pressure in this region. At this time, the irrigation solution pressed by the tint corner 201 moves toward the second corner 202 side along the first surface 221 with the rotation of the fragmentation tip 2. This eliminates the negative pressure generated in the vicinity of the second corner 202. The same phenomenon occurs also around the second surface 222, so that a negative pressure generated in the vicinity of the fourth corner 204 is eliminated by the irrigation solution flowing from the third corner 203 along the second surface 222. In this rotation in the positive direction R1, the first corner 201 and the third corner 203 apply shock to the nucleus, so as to fragment the nucleus.

Subsequently, when the fragmentation tip 2 rotates in the reverse direction R2 from the state of FIG. 5(a) to the state of FIG. 5(b), the first corner 201 that is one end of the first surface 221 rotates in a direction away from the irrigation solution, and therefore a negative pressure is generated in the vicinity thereof. However, the irrigation solution having a positive pressure flows from the vicinity of the second corner 202 toward the first corner 201, and thus the negative pressure in the vicinity of the first corner 201 is eliminated. On the other hand, the third corner 203 that is one end of the second surface 222 rotates in a direction away from the irrigation solution, and therefore a negative pressure is generated in the vicinity thereof. However, the irrigation solution having a positive pressure flows from the fourth corner 204 toward the third corner 203, and thus the negative pressure in the vicinity of the third corner 203 is eliminated. It should be noted that, at the time of rotation in the reverse direction R2, the second corner 202 and the fourth corner 204 apply shock to the nucleus, so as to fragment the nucleus. While repeating the above movement, each of the corners 201 to 204 applies shock to the nucleus, so as to fragment the nucleus.

As described above, according to this embodiment, the tip body 22 is formed to have a rectangular cross section, and therefore the irrigation solution is allowed to flow from a positive pressure region formed at one end of the first surface 221 to a negative pressure region formed at the other end of the first surface 221. That is, the irrigation solution in the positive pressure region flows along the first surface 221 with the rotation, and moves to the negative pressure region. This eliminates the negative pressure. Such a phenomenon occurs also around the second surface 222, and therefore it is possible to prevent formation of negative pressure regions in the peripheral irrigation solution during the rotation of the fragmentation tip 2. As a result, it is possible to suppress cavitation, thereby preventing damage to the eyeball such as the iris.

Further, while the fragmentation tip 2 rotates back and fourth one time each of the corners 201 to 204 can apply shock to the nucleus, which makes it possible to fragment the nucleus efficiently. Furthermore, the tip body 22 is formed to have a narrow rectangular cross sectional shape, which facilitates insertion into nuclear fibers of the lens. Further, the arcuate protruding portions 2230 and 2240 are formed on the third surface 223 and the fourth surface 224. Since these protruding portions 2230 and 2240 are curved along the rotational direction of the fragmentation tip 2, no negative pressure occurs in these regions. Further, there is less resistance to the irrigation solution, and thus it is possible to prevent an increase in resistance to the rotation of the fragmentation tip 2.

In the aforementioned embodiment, the tip body 22 has a rectangular cross section. However, there is no limitation to this. That is, the aforementioned effects can be obtained as long as the tip body 22 has a point-symmetrical cross sectional shape having a length in the longitudinal direction (the first direction) larger than a length in the width direction (the second direction) that is orthogonal to the aforementioned direction. Accordingly, it is possible to employ various shapes such as an ellipsoidal shape and a diamond shape, for example, rather than a rectangular shape having no protruding portions on the third surface 223 and the fourth surface 224.

Fragmentation Tip: Second Embodiment

Figure 6:
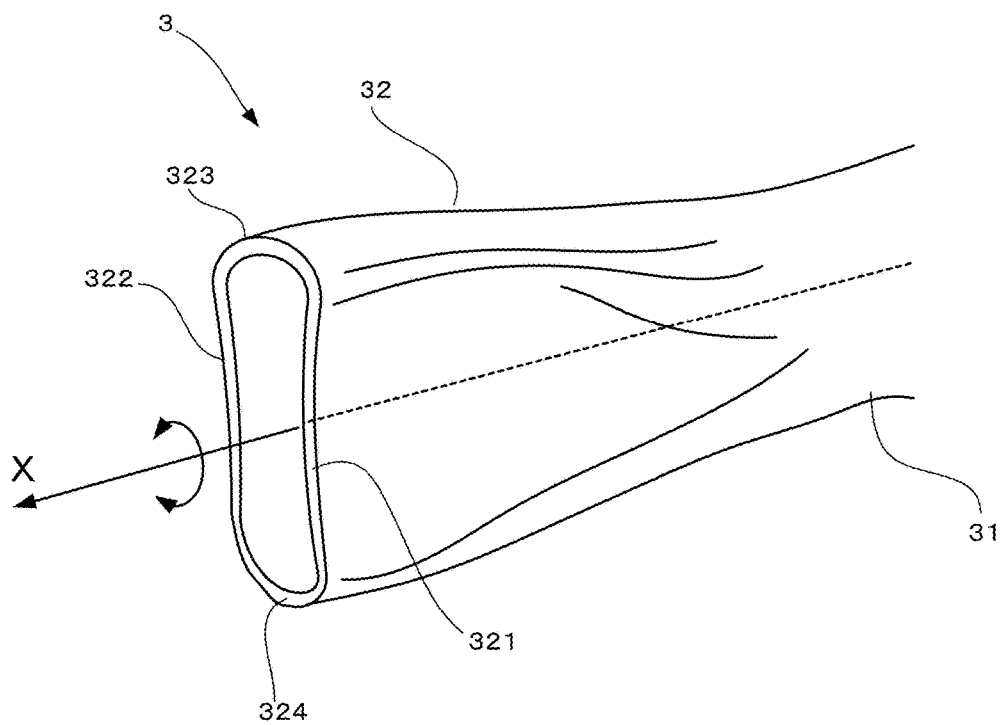
FIG. 6 is a perspective view showing a second embodiment of a fragmentation tip configured to be mounted on the handpiece in FIG. 1.
Figure 7:
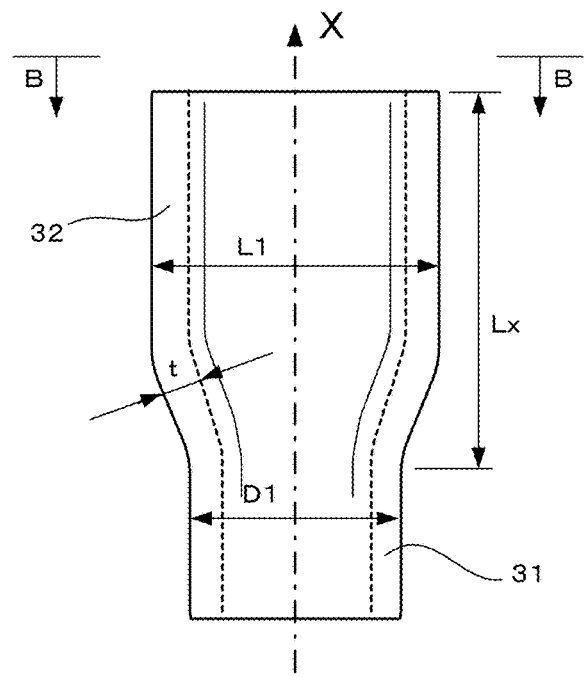
FIG. 7 is a side view of the fragmentation tip in FIG. 6.
Figure 8:
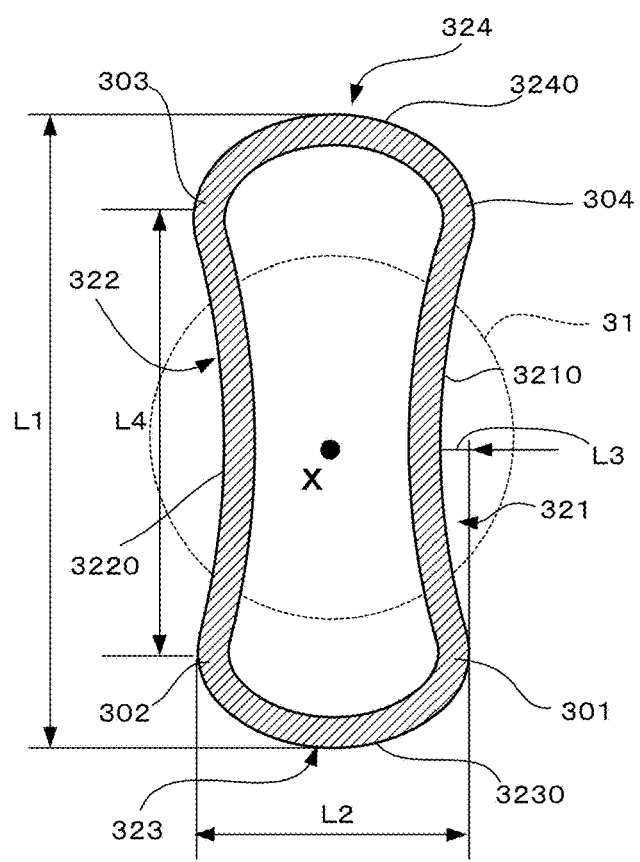
FIG. 8 is a view taken along the line B-B in FIG. 7 as seen in the direction of the arrows.

Next, a second embodiment of as fragmentation tip will be described in detail with reference to FIG. 6 to FIG. 8. FIG. 6 is a perspective view of the fragmentation tip according to the second embodiment, FIG. 7 is a side view of FIG. 6, and FIG. 8 is a view taken along the line B-B in FIG. 7 as seen in the direction of the arrows. Hereinafter, a direction in which the fragmentation tip extends from the body 1 is referred to as axis direction X, and a direction that extends radially from the axis is referred to as radial direction.

As shown in FIG. 6, a fragmentation tip 3 is formed of metal, or the like, and is composed of a support portion 31 that is attached to the distal end of a body 11 and extends cylindrically and a tip body 32 that is integrally attached to the distal end of the support portion 31 and is configured to fragment a lens nucleus. The support portion 31 and the tip body 32 are formed together into a tubular shape as a whole, as described above, through which the fragmented lens nucleus and the irrigation solution pass. That is, a flow channel is formed that extends from the opening at the distal end of the tip body 32 through the tip body 32 and the support portion 31.

The tip body 32 is formed into an approximate rectangular cuboid having a point-symmetrical rectangular cross section, and the aforementioned axis X extends through the center of point symmetry of the rectangular cross section. Here, opposing surfaces corresponding to the long sides of the rectangular shape are referred to as a first surface 321 and a second surface 322, and opposing surfaces corresponding to the short sides thereof are referred to as a third surface 323 and a fourth surface 324. Further, as shown in FIG. 7 and FIG. 8, a long side length L1 is formed to be larger than a diameter D1 of the support portion 31, and a short side length L2 is formed to be smaller than the diameter D1 of the support portion 31. Further, a material thickness t of the tip body 32 and the support portion 31 may be approximately constant or may be varied. The size of the tip body 32 is appropriately determined depending on the surgical form. For example, the long side length L1 may be 0.9 to 1.727 mm, and the short side length L2 may be 0.24 to 1.1 mm. Further, a length Lx of the tip body 32 in its axis direction, for example, may be 1 to 5 mm.

Next, the cross sectional shape of the tip body 32 will be described further in detail with reference to FIG. 8. First, as shown in this figure, the long side length L1 is preferably about 1 to 7 times, or more preferably 2 to 5 times, the short side length L2. This is because if the cross section of the tip body 32 is a square-like shape, it is difficult to insert the tip body 32 into nuclear fibers of a lens nucleus. On the other hand, this is also because, in the case of an excessively narrow shape, processing is difficult, and aspiration of the irrigation solution is also difficult. On the first surface 321 and the second surface 322, arcuate recessed portions 3210 and 3220 recessed inwardly in the radial direction are respectively formed. On the third surface 323 and the fourth surface 324, arcuate protruding portions 3230 and 3240 projecting outwardly in the radial direction are respectively formed. Further, coupled portions of adjacent surfaces form corners (projections) that project outward in the radial direction. Here, the coupled portion between the first surface 321 and the third surface 323 is referred to as a first corner 301, the coupled portion between the third surface 323 and the second surface 322 is referred to as a second corner 302, the coupled portion between the second surface 322 and the fourth surface 324 is referred to as a third corner 303, and the coupled portion between the fourth surface 324 and the first surface 321 is referred to as a fourth corner 304.

Next, a cataract surgery method using a handpiece configured as above will be described. A cataract surgery is mainly composed of the following four steps. That is, there are steps of (1) incision of anterior capsule, (2) emulsification and aspiration of nucleus, (3) aspiration of cortex, and (4) insertion of intraocular lens, among which steps (1) and (2) are mainly described herein. In step (1), while maintaining the shape of the anterior chamber using a viscoelastic material, for example, the anterior capsule is first incised. In step (2), incision layers are firmed in the cornea and sclera, and the fragmentation tip 2 is inserted into the anterior chamber so that the nucleus is fragmented and emulsified by the vibration of the fragmentation tip 3. The emulsified nucleus is aspirated through the opening at the distal end of the fragmentation tip 3 together with the irrigation solution, and is discharged from the port 11 to the outside through the discharge channel in the handpiece. The anterior chamber is kept stable by maintaining a balance between the inflow amount of the irrigation solution and the aspiration amount.

Figure 9:
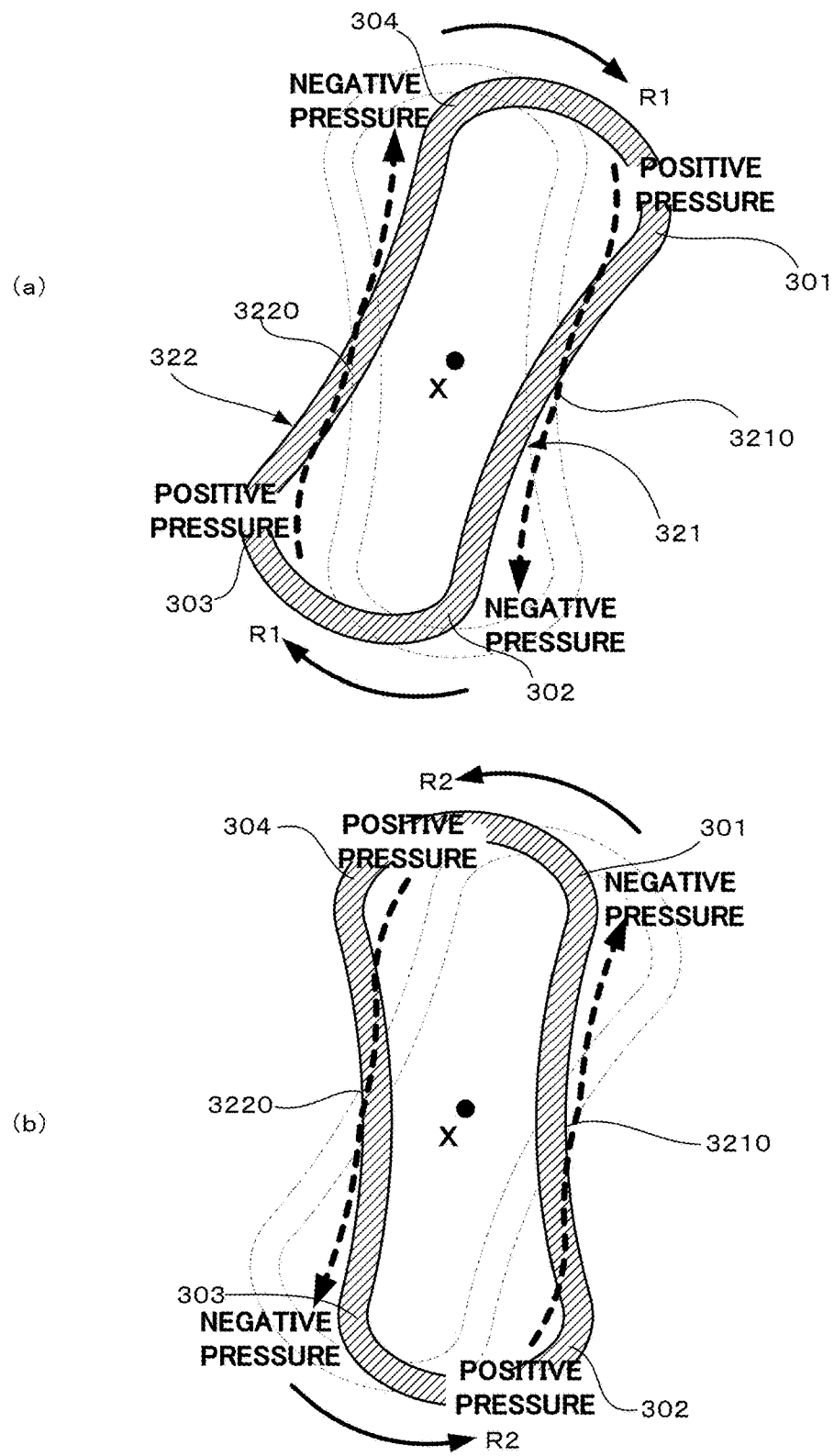
FIG. 9 is an explanatory diagram illustrating a movement of the fragmentation tip in FIG. 6.

Subsequently, the movement of the fragmentation tip 3 will be described with reference to FIG. 9. The cataract surgery is as described in the first embodiment. Hereinafter, the clockwise direction in FIG. 9 is referred to as positive direction R1, and the counterclockwise direction is referred to as reverse direction R2. As described above, when ultrasonic vibration is applied to the fragmentation tip 2, the fragmentation tip rotates back and forth about the axis X. Specifically, the fragmentation tip rotates in the positive direction R1 at the aforementioned angle, thereby transferring the state from the state of FIG. 8 to the state of FIG. 9(a), and then the fragmentation tip rotates in the reverse direction R2 at the same angle, thereby trans rung the state from the state of FIG. 9(a) to the state of FIG. 9(b), and this movement is repeated. First, when the fragmentation tip 2 rotates in the positive direction R1 from the state of FIG. 8 to the state of FIG. 9(a), one end of the first surface 321, that is, the first projection 301 rotates so as to press the irrigation solution, which causes a positive pressure in this region. On the other hand, the other end of the first surface 321, that is, the second projection 302 moves in a direction away from the irrigation solution, which causes a negative pressure in this region. However, since the arcuate recessed portion 3210 is formed on the first surface 321, the irrigation solution pressed by the first corner 301 flows into the recessed portion 3210 with the rotation of the fragmentation tip 2, and moves toward the second corner 302 side. This eliminates the negative pressure generated in the vicinity of the second projection 302. The same phenomenon occurs also around the second surface 322, so that a negative pressure generated in the vicinity of the fourth corner 304 is eliminated by the irrigation solution flowing from the third corner 303 into the recessed portion 3210. In this rotation in the positive direction R1, the first corner 301 and the third corner 303 apply shock to the nucleus, so as to fragment the nucleus.

Subsequently, when the fragmentation tip 3 rotates in the reverse direction R2 from the state of FIG. 9(a) to the state of FIG. 9(b), the first corner 301 that is one end of the first surface 321 rotates in a direction away from the irrigation solution, and therefore a negative pressure is generated in the vicinity thereof. However, the irrigation solution having a positive pressure flows from the vicinity of the second corner 302 toward the first corner 301 along the recessed portion 3210, and thus the negative pressure in the vicinity of the first corner 301 is eliminated. On the other hand, the third corner 303 that is one end of the second surface 322 rotates in a direction away from the irrigation solution, and therefore a negative pressure is generated in the vicinity thereof. However, the irrigation solution having a positive pressure flows from the fourth corner 304 toward the third corner 303 along the recessed portion 3220, and thus the negative pressure in the vicinity of the third corner 303 is eliminated. It should be noted that, at the time of rotation in the reverse direction R2, the second corner 302 and the fourth corner 304 apply shock to the nucleus, so as to fragment the nucleus. While repeating the above movement, each of the corners 301 to 304 applies shock to the lens, so as to fragment the lens.

As described above, according to this embodiment, the tip body 32 is formed to have a rectangular cross section, and the recessed portions 3210 and 3220 are respectively formed on the first surface 321 and the second surface 322 that constitute the long sides. Therefore, it is possible to allow the irrigation solution to flow from positive pressure regions formed at one end of the recessed portion 3210 and one end of the recessed portion 3220 to negative pressure regions formed at the other end of the recessed portion 3210 and the recessed portion 3220. That is, the irrigation solution in the positive pressure regions flows into the recessed portions 3210 and 3220 with the rotation, and moves to the negative pressure regions. Thus, negative pressure is eliminated, and it is possible to prevent formation of negative pressure regions in the peripheral irrigation solution during the rotation of the fragmentation tip 3. As a result, it is possible to suppress the occurrence at cavitation, thereby preventing damage to the eyeball in areas such as the iris.

Meanwhile, in order to suppress the occurrence of cavitation, it is necessary to allow the irrigation solution to flow from a positive pressure side to a negative pressure side along the recessed portions 3210 and 3220, as described above. However, if a depth (the distance from the outermost portion in the short side direction) L3 of the recessed portions 3210 and 3220 is excessively large, there is a risk that it will be difficult for the irrigation solution to flow smoothly, and if it is excessively small, there is a risk that it will be impossible for the irrigation solution to flow. From such a viewpoint, the depth L3 of the recessed portions 3210 and 3220 is preferably about 2 to 40%, and more preferably 2 to 20%, of the short side length L2. Further, if a length L4 of the recessed portions 3210 and 3220 is excessively small, it is impossible for the irrigation solution to flow to the negative pressure side sufficiently, and if it is excessively large, it is impossible to form the protruding portions 3230 and 3240 of the third surface 323 and the fourth surface 324. From such a viewpoint, the length L4 of the recessed portions 3210 and 3220 in the long side direction of the tip body 32 is preferably 10 to 60%, further preferably 40 to 60%, with respect to the long side length L1. It should be noted that the length L2 of the recessed portions 3210 and 3220 is generally defined with the aforementioned projections 301 to 304 serving as the two ends thereof.

Further, while the fragmentation tip 3 rotates back and forth one time, each of the corners 301 to 304 can apply shock to the nucleus, which makes it possible to fragment the nucleus efficiently. Furthermore, the tip body 32 is formed to have a narrow rectangular cross sectional shape, which facilitates insertion into nuclear fibers of the nucleus. Further, the arcuate protruding portions 3230 and 3240 are formed on the third surface 323 and the fourth surface 324. Since these protruding portions 3230 and 3240 are curved along the rotational direction of the fragmentation tip 3, no negative pressure occurs in these regions. Further, there is less resistance to the irrigation solution, and thus it is possible to prevent an increase in resistance to the rotation of the fragmentation tip 3.

Figure 10:
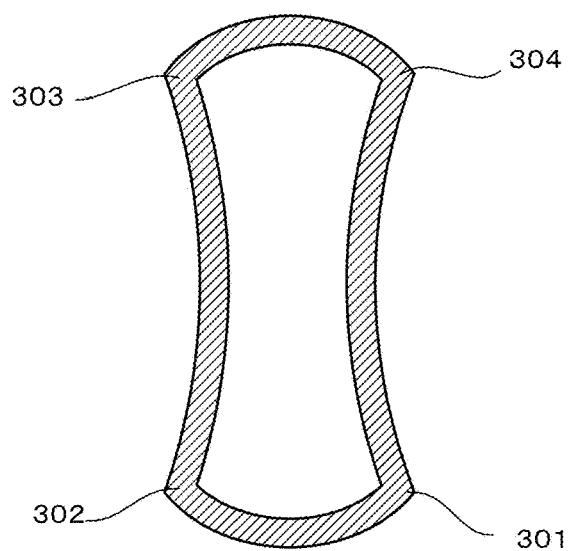
FIG. 10 is a front view showing another example of the fragmentation tip in FIG. 6.
Figure 11:
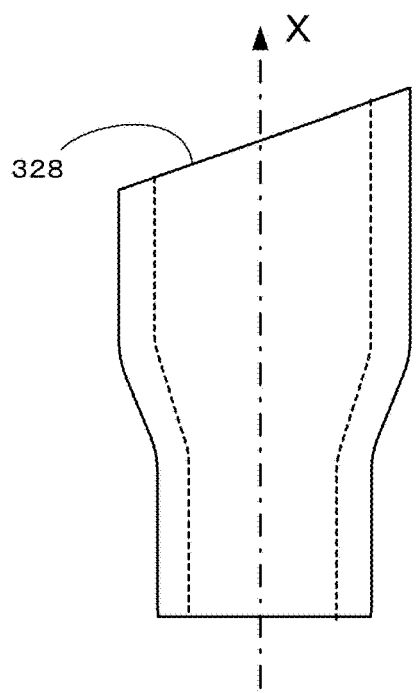
FIG. 11 is a side view showing another example of the fragmentation tips in FIG. 2 and FIG. 6.

Hereinbefore, embodiments of the present invention have been described. However, the present invention is not limited to the aforementioned embodiments, and various modifications can be made without departing from the gist of the present invention. For example, in the aforementioned second embodiment, as shown in FIG. 8, each of the corners 301 to 304 of the tip body is formed of a curved surface, which can be formed of a sharp corner, for example, as shown in FIG. 10. Further, in the examples shown in FIG. 3 and FIG. 7, the opening at the distal end of the tip body is rectangular to the axis X. However, the opening 328 may be inclined, for example, as shown in FIG. 11. The support portions 21 and 31 may have a rectangular cylindrical shape rather than a circular cylindrical shape. Further, in the aforementioned embodiments, the axis X of the support portions 21 and 31 passes through the center of the cross section of the tip bodies 22 and 32. However, the axis X does not necessarily pass through the center, and may be deviated from the center or may be slightly inclined from the direction in which the tip bodies 22 and 32 extend.

The aforementioned tip bodies 22 and 32 each have a cross section with long sides and short sides. However, the tip bodies may have various shapes as long as a length in one direction (a first direction) is larger than a length in a width direction (a second direction) that is orthogonal to the first direction. In particular, a cross sectional shape that is linearly symmetrical is preferable, and a point-symmetrical cross sectional shape is further preferable. Specifically, an ellipsoidal shape, a rhombic shape, or the like can be employed, for example, in addition to the rectangular shape and the gourd shape mentioned above.

EXAMPLES

Figure 12:
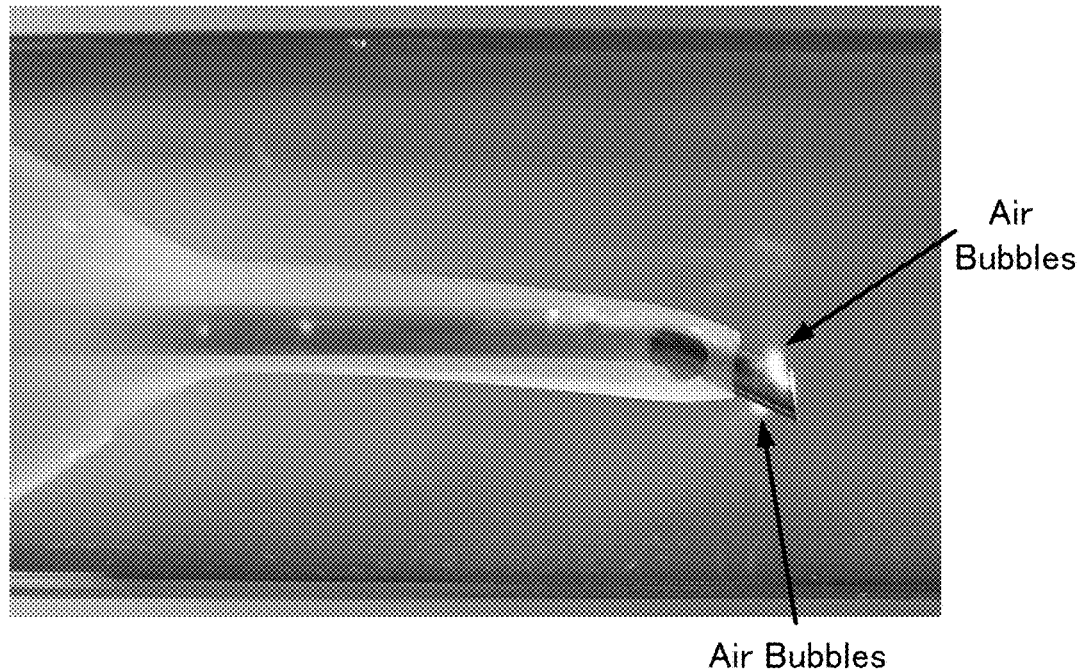
FIG. 12 is a photograph showing a test to check the occurrence of cavitation using a comparative example.

Hereinafter, examples of the present invention will be described. However, the present invention is not limited to the following examples. Fragmentation, tips according to three types of examples and one type of a comparative example have been produced herein for checking the occurrence of cavitation. Each example had the aforementioned cross section of FIG. 8, in which a fragmentation tip having a distal end inclined a 30 degrees as shown in FIG. 11 was produced. On the other hand, the comparative example is a fragmentation tip composed of a cylindrical support portion connected to a handpiece, and a distal end portion that is bent at the distal end of the support portion, as shown in FIG. 12. The shape of the fragmentation tip according to each example is shown below.

TABLE 1

|  | L1 | L2 | L3 | L4 | Lx | D1 |
|---|---|---|---|---|---|---|
| Example 1 (New type) | 1.38 | 0.62 | 0.015 | 0.76 | 2.80 | 1.10 |
| Example 2 (with a small curvature) | 1.47 | 0.53 | 0.065 | 0.76 | 2.80 | 1.10 |
| Example 3 (with an intermediate curvature) | 1.53 | 0.50 | 0.080 | 0.76 | 2.80 | 1.10 |

(Unit: mm)

Further, in the comparative example, the diameter was 0.9 mm, the angle of the distal end was 30 degrees, and the bending angle of the bent distal end was 20 degrees.

Figure 13:
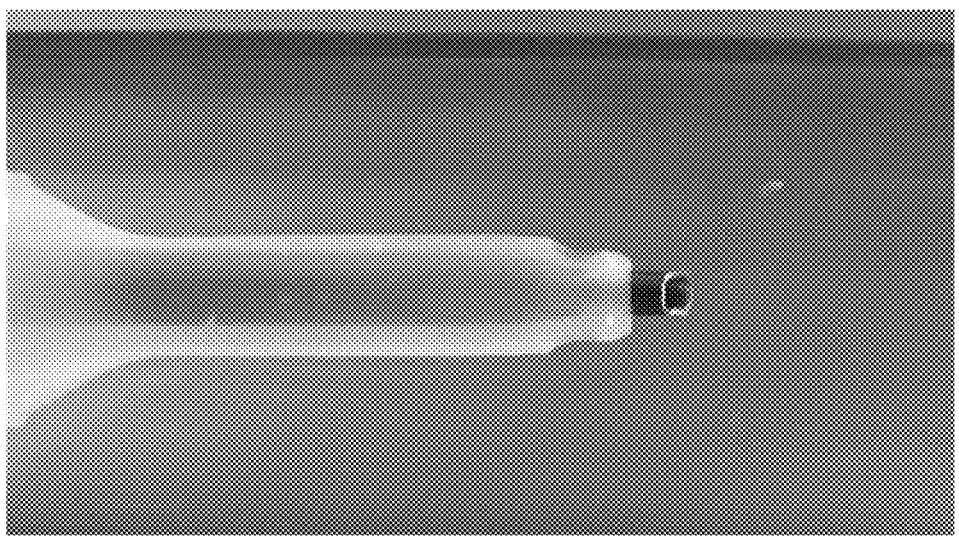
FIG. 13 is a photograph showing a test to check the occurrence of cavitation using Example 1.
Figure 14:
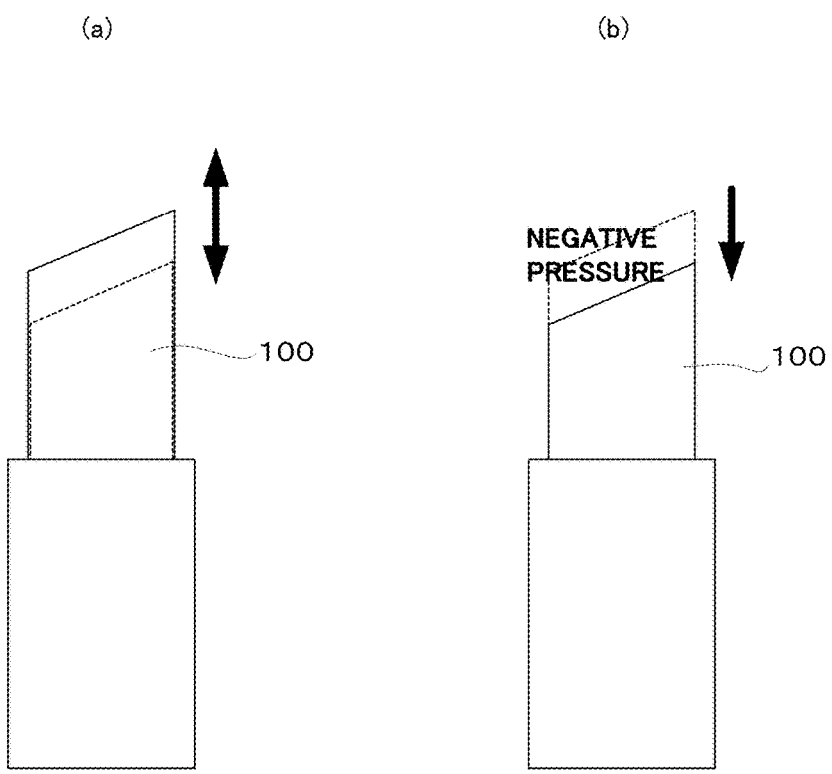
FIG. 14 is a side view showing a conventional fragmentation tip.

The fragmentation tip according to the examples and the comparative example is mounted on a handpiece, and vibration is applied in water. Thus, the occurrence of cavitation was checked. The fragmentation tips of the examples were subjected to about 32000 back-and-forth rotations per minute with a rotation angle of about 4 (2+2) degrees. On the other hand, the support portion of the comparative example was subjected to about 32000 back-and-forth rotations per minute at a rotation angle of about 4 (2+2) degrees about its axis. Thus, the bent distal end portion is allowed to rotate back and forth about the axis. As a result, cavitation occurred in none of the examples, whereas cavitation occurred in the comparative example. FIG. 12 is a photograph showing a test situation using the comparative example. FIG. 13 is a photograph showing a test situation using Example 1. From these photographs the following can be seen. In the comparative example, back-and-forth rotation of the distal end portion causes a negative pressure continuously, resulting in generation of air bubbles at the distal end of the fragmentation tip. That is cavitation occurred. On the other hand, air bubbles are not generated in Example 1. That is, cavitation did not occur.

REFERENCE SIGNS LIST

1: Body
2, 3: Fragmentation Tip
21, 31: Support portion
22, 32: Tip Body
221, 321: First Surface
2210, 3210: Recessed Portion
222, 322: Second Surface
2220, 3220: Recessed Portion 223, 323: Third Surface
2230, 3230: Protruding Portion
224, 324: Fourth Surface
2240, 3240: Protruding Portion

The invention claimed is:

1. A fragmentation tip, which is attached to an intraocular surgery device configured to apply ultrasonic vibration, comprising:
   a cylindrical support portion configured to be mounted on the intraocular surgery device; and
   a tip body provided at a distal end of the support portion so as to be in communication with an internal space of the support portion,
   wherein the tip body has a point-symmetrical cross sectional shape having a length in a first direction larger than a length in a second direction that is orthogonal to the first direction,
   the tip body has a first surface and a second surface which oppose each other extending along the first direction, and a third surface and a fourth surface which oppose each other extending along the second direction, the lengths of the first and second surfaces being larger than the lengths of the third and fourth surfaces,
   arcuate recessed portions are formed on the first surface and the second surface,
   arcuate protruding portions form each of the entire third and fourth surfaces, and
   vibration is applied to the support portion so that the tip body rotates back and forth about an axis of the tip body that passes through its center in the first direction and the second direction.

2. The fragmentation tip according to claim 1, wherein the tip body has the length in the first direction that is two or more times the length in the second direction.

3. An intraocular surgery device comprising:
   a body configured to be supported by a hand of an operator;
   a vibration generator incorporated in the body and configured to generate ultrasonic vibration; and
   the fragmentation tip according to claim 1 which is configured to be coupled to a distal end of the body so as to be vibrated by the vibration generator, wherein
   vibration is applied to the fragmentation tip by the vibration generator so that the fragmentation tip rotates back and forth about the axis of the tip body that passes through its center in the first direction and the second direction.

4. A method for suppressing an occurrence of cavitation, comprising the steps of:
   preparing the fragmentation tip according to claim 1; and
   applying ultrasonic vibration to the fragmentation tip so that the tip body rotates back and forth about the axis of the tip body that passes through its center in the first direction and the second direction.

5. A cataract surgery method comprising the steps of:
   attaching the fragmentation tip according to claim 1 to an intraocular surgery device configured to apply ultrasonic vibration;
   applying ultrasonic vibration to the fragmentation tip so that the tip body rotates back and forth about the axis of the tip body that passes through its center in the first direction and the second direction; and
   a step of fragmenting a lens of an eye of a cataract patient by applying shock to the lens using the fragmentation tip, while supplying an irrigation solution to the eye of the patient.

* * * * *